United States Patent
Pyerin et al.

[11] Patent Number: 5,948,901
[45] Date of Patent: Sep. 7, 1999

[54] ANTISENSE OLIGONUCLEOTIDES FOR AROMATASE INHIBITION

[75] Inventors: Walter Pyerin, Heidelberg; Karin Ackermann, Ladenburg; Jürgen Fauss, Waldsee, all of Germany

[73] Assignee: Deutsches Krebsforschungszentrum Stiftung Des Öffentlichen Rechts, Germany

[21] Appl. No.: 08/605,190

[22] PCT Filed: Jun. 23, 1995

[86] PCT No.: PCT/EP95/02461

§ 371 Date: Aug. 13, 1996

§ 102(e) Date: Aug. 13, 1996

[87] PCT Pub. No.: WO96/00231

PCT Pub. Date: Jan. 4, 1996

[30] Foreign Application Priority Data

Jun. 24, 1994 [DE] Germany .............................. 44 22 259

[51] Int. Cl.[6] .......................... C07H 21/04; A61K 48/00
[52] U.S. Cl. ............................................. 536/24.5; 514/44
[58] Field of Search .................................. 536/24.5, 25.3; 514/44

[56] References Cited

U.S. PATENT DOCUMENTS 5,585,479  12/1996  Hoke et al. ............................ 536/24.5

OTHER PUBLICATIONS

Stein CA, et al. "Antisense oligonucleotides as therapeutic agents—Is the bullet really magical?" Science 261: 1004–1012, Aug. 20, 1993.

Gura T. "Antisense has growing pains." Science 270: 575–577, Oct. 27, 1995.

Rojanasakul Y. "Antisense oligonucleotide therapeutics: Drug delivery and targeting." Adv. Drug Delivery Rev. 18: 115–131, 1996.

Stull RA, et la. "Antigene, ribozyme and aptamer nucleic acid drugs: Progress and prospects." Pharmaceutical Res. 12: 465–483, 1995.

Ackermann et al, 1994, "Inhibition Of Cyclic AMP–Triggered Aromatase Gene Expression In Human Choriocarcinoma Cells By Antisense Oligodeoxynucleotide," *Cancer Research* 54:4940–4946.

Bradford, 1976, "A Rapid And Sensitive Method For The Quantitation Of Microgram Quantities Of Protein Utilizing The Principle Of Protein–Dye Binding," *Anal. Biochem.* 72:248–254.

Ellis et al., 1993, "Design And Specificity Of Hammerhead Ribozymes Against Calretinin mRNA," *Nucleic Acids Res.* 21:5171–5178.

Fauss et al., 1993, "Rapid Assay Of Aromatase Activity By Fast Liquid Chromatography: Spectroscopic Evaluation Of Metabolite Profiles Indicate Unexpected Pitfalls," *Analytical Biochemistry* 210:421–423.

Hélène et al., 1990, "Specific Regulation Of Gene Expression By Antsense, Sense and Antigene Nucleic Acids," *Biochim. Biophys. Acta* 1049:99–125.

Mahendroo et al., 1993, "Tissue–Specific And Hormonally Controlled Alternative Promoters Regulate Aromatase Cytochrome P450 Gene Expression In Human Adipose Tissue," *J. Biol. Chem.* 268:19463–19470.

Nebert et al., 1987, "P450 Genes: Structure, Evolution, And Regulation," *Ann. Rev. Biochem.* 56:945–993.

Stein et al., 1988, "Oligodeoxynucletides As Inhibitors Of Gene Expression: A Review," *Cancer Research* 48:2659–2668.

*Primary Examiner*—Nancy Degen
*Assistant Examiner*—Janet Epps
*Attorney, Agent, or Firm*—Pennie & Edmonds LLP

[57] ABSTRACT

The invention relates to an antisense oligonucleotide suitable for inhibiting the expression of aromatase, the antisense oligonucleotide being obtainable by the following steps:

(a) construction of antisense oligonucleotides along the entire length of coding and regulatory regions of an aromatase DNA and/or transcripts thereof, the antisense oligonucleotides overlapping;

(b) incubation of an aromatase-expressing cell with one or more of the antisense oligonucleotides of (a); and (c) detection of the inhibition of the aromatase expression as usual, as well as identification of the antisense oligonucleotide(s) responsible for this. Furthermore, the invention relates to a process for preparing such an antisense oligonucleotides as well as its use.

2 Claims, 2 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:1:

TTCTACCAAA ACCTTTACGA          20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

CCTCCCGACT TGTGCACCTC          20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:3:

GTAGTCTCTC GGAGGGGAGG          20

(2) INFORMATION FOR SEQ ID NO:4:

(i) SEQUENCE CHARACTERISTICS:
      (A) LENGTH: 43 base pairs
      (B) TYPE: nucleic acid
      (C) STRANDEDNESS: single
      (D) TOPOLOGY: linear -continued (xi) SEQUENCE DESCRIPTION: SEQ ID NO:4:

GTCAAGGAAC ACAAGATGTT TTGGAAATGC TGAACCCGAT ACA                43

ANTISENSE OLIGONUCLEOTIDES FOR AROMATASE INHIBITION

I. FIELD OF THE INVENTION

The invention relates to antisense oligonucleotides which are suitable for inhibiting the expression of aromatase, a process for the production thereof as well as their use.

II. BACKGROUND OF THE INVENTION

Aromatase belongs to the cytochrome p450 enzyme family. Aromatase is the key enzyme in the estrogen biosynthesis. It converts the male sex hormones (androgens) into the female ones (estrogens). The latter are growth factors for a plurality of tumors, particularly those of ovaries, endometrium and breast.

For treating the above tumors, it is tried to inhibit the estrogen biosynthesis. Aromatase inhibitors are often used for this purpose. However, they have not shown satisfactory results by now, particularly they are lacking specificity.

Therefore, it is the object of the present invention to provide a preparation by which aromatase can be inhibited specifically.

According to the invention this is achieved by providing an antisense oligonucleotide which prevents the expression of aromatase by attachment to aromatase DNA and/or mRNA. The expression "antisense" is generally known and refers to a complementarily of the oligonucleotide sequence to the region of aromatase DNA and/or mRNA.

III. SUMMARY OF THE INVENTION

The present invention is directed to an antisense oligonucleotide suitable for inhibiting the expression of aromatase, the antisense oligonucleotide being obtainable by the following steps:

(a) construction of antisense oligonucleotides along the entire length of coding and regulatory regions of an aromatase DNA and/or transcripts thereof, the antisense oligonucleotides overlapping;

(b) incubation of an aromatase-expressing cell with one or more of the antisense oligonucleotides of (a); and (c) detection of the inhibition of the aromatase expression as usual, as well as identification of the antisense oligonucleotide(s) responsible for this.

The present invention also directed to a process for preparing such an antisense oligonucleotides as well to methods for its use.

IV. BRIEF DESCRIPTION OF THE DRAWINGS

V. DESCRIPTION OF THE INVENTION

Figure 1A:
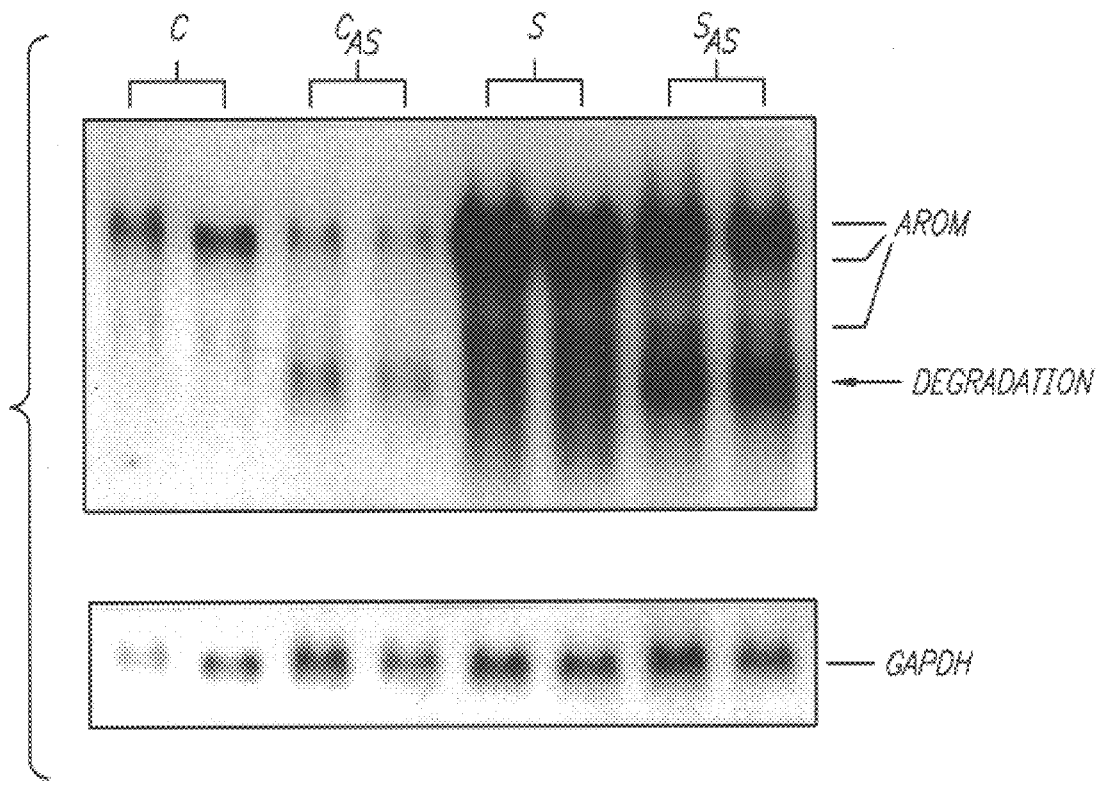
FIG. 1A depicts a Northern Blot reflecting the effect of an antisense oligonucleotide according to the invention on the expression of aromatase mRNA.

An antisense oligonucleotide according to the invention can be prepared as usual. A process proves to be favorable which comprises the following steps:

(a) construction of antisense oligonucleotides along the entire length of coding and regulatory regions of aromatase DNA and/or transcripts thereof, the antisense oligonucleotides overlapping;

(b) incubation of an aromatase-expressing cell with one or more of the antisense oligonucleotides of (a); and (c) detection of the inhibition of the aromatase expression as usual, as well as identification of the antisense oligonucleotide(s) responsible for this.

An antisense oligonucleotide according to the invention may have differing lengths. Lengths of 20 to 30 nucleotides are preferred. Furthermore, the antisense oligonucleotide may have variations in its sugar and phosphate components each. The sugar component conceivable is deoxyribose, ribose or a chemical variant thereof, for example. The phosphate component may be, e.g., ortho-phosphoric acid diester or a chemical variant thereof. A preferred antisense oligonucleotide contains deoxyribose as sugar component and ortho-phosphoric acid diester as phosphate component.

In the above step (a), antisense oligonucleotides are constructed along the entire length of coding and regulatory regions of an aromatase DNA and/or transcripts thereof. An aromatase DNA and transcripts thereof are known from Mahendroo et al., 1993, *J. Biol. Chem.*$_{13}$:19463–19470, for example. Such a DNA comprises 9 coding exons (exons II–X). Furthermore, several exons I (exons I.1.I.4) exist which are non-coding, transcribed in tissue-specific manner and thus have regulatory functions. The various aromatase transcripts (mRNA) are equal in the translated region (exons II–X) but differ in a tissue-specific manner in the 5' untranslated region (exon I).

Antisense oligonucleotides are constructed as usual. It is favorable to construct them in overlapping fashion. This facilities the localization of sequences inhibiting an aromatase expression. Also, such sequences are to be searched for especially in exon II (5' translated region of mRNA) and exons I.1–I.4 (5' untranslated region of mRNA) of an aromatase DNA as well as in the 3' untranslated region of an aromatase mRNA.

A preferred antisense oligonucleotide is one having a partial sequence of exon II of an aromatase DNA, particularly preferably with the following sequence:

3'-TTCTACCAAAACCTTTACGA-5' (SEQ ID NO:1)

Another preferred antisense oligonucleotide is one having a partial sequence of exon I.1 of an aromatase DNA, particularly preferably with the following sequence:

3'-CCTCCCGACTTGTGCACCTC-5' (SEQ ID NO:2).

Another preferred antisense oligonucleotide is one having a partial sequence of exon I.2 of an aromatase DNA, particularly preferably with the following sequence:

3-GTAGTCTCTCGGAGGGGAGG-5' (SEQ ID NO:3).

Further preferred antisense oligonucleotides are those having in each case one partial sequence of exon I.3 and exon I.4 respectively, of an aromatase DNA. Also, an antisense oligonucleotide which has a partial sequence of the 3' un translated region of an aromatase mRNA is preferred.

The sequence of an antisense oligonucleotide according to the invention may be fully complementary to the sequence, to be bonded, of an aromatase DNA and/or mRNA. On the other hand, the antisense oligonucleotide may also contain one or more nucleotides which are not complementary to the corresponding nucleotides of the sequence to be bonded. In addition, the antisense oligonucleotide may have a sequence encoding for a functionality such as RNase activity. Ellis and Rogers, 1993, *Nucleic Acids Res.* 21:5171–5178. Such an antisense oligonucleotide shows in an especially advantageous manner when the bonded aromatase mRNA is decomposed. It also represents a subject matter of the present invention.

In the above step (b), an aromatase-expressing cell is incubated with one or more of the antisense oligonucleotides according to the invention. The resulting inhibition of the aromatase expression is then detected, and the antisense oligonucleotide(s) responsible for the inhibition are identified (above step (c)).

The expression "aromatase-expressing cell" comprises any cells and cell agglomerations capable of expressing aromatase. They include, e.g., cells of human placenta, furthermore cells of gonads and adipose tissue as well as the corresponding organs and tissues as such. Cells of the choriocarcinoma cell line JEG-3 are preferred. This cell line is obtainable from the American Type Culture Collection under HTB 36.

An aromatase expression is detected by common methods. They include, e.g., determinations of the aromatase activity, testosterone or androstenedione, for example, being used as the substrate and the formation of 17β-estradiol (E2) being determined, see, Example 2, infra, of the aromatase protein via the method of Bradford, 1976, *Anal. Biochem.* 72:248–254, followed by Western blot, or of the aromatase mRNA in a Northern blot, a DNA sample specific to aromatase mRNA, e.g., cDNA, being used. See, Example 2, infra.

The expression of aromatase is effected in the above cells or cell agglomerations by induction and enhanced in the case of JEG-3 cells, respectively. For this purpose, it is possible to use conventional adenylate cyclase stimulators, e.g,. human chorio gonadotrophin (hCG), or membrane-permeating analogues of cyclic AMP (cAMP) such as dibutyryl cAMP (dbcAMP). The individual concentrations are determined by a person skilled in the art by means of standard tests or follow from the literature. Nebert and Gonzales, 1987, *Ann. Rev. Biochem.* 56:945–993.

The above cells or cell agglomerations are incubated with one or more of the antisense oligonucleotides according to the invention as usual. The individual concentrations are determined by the person skilled in the art by means of standard tests. Furthermore, the aromatase expression-inhibiting effect of the antisense oligonucleotide(s) can be determined directly. The difference from the aromatase expression of cells or symplasms incubated with and without antisense oligonucleotides is employed for this purpose. The aromatase expression is determined as described above.

Antisense oligonucleotides according to the invention are perfectly suitable for the inhibition of aromatase expression. Thus, they represent preparations for inhibiting the estrogen biosynthesis in well-calculated fashion. This offers new possibilities of being able to treat by means of gene therapy various diseases linked with the estrogen biosynthesis, particularly tumor diseases.

Antisense oligonucleotides according to the invention can be given a person as such, individually or in combination. However, they can also be expressed within the person by means of an expression vector containing sequences encoding for them.

The invention is explained by the examples. The following preparations and examples are given to enable those skilled in the art to more clearly understand and to practice the present invention. The present invention is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Construction of an Antisense Oligonucleotide

In the region of nucleotides 36–55, an aromatase mRNA comprising the 5'-translated region (exon II) includes the following sequence:

5'-GTCAAGGAACACAAGATGTTTTGGAAAT-GCTGAACCCGATACA-3' (SEQ ID NO:4).

As far as this sequence is concerned, an antisense oligonucleotide of the following sequence was constructed. A generally available synthesis apparatus (Applied Biosystems) was used:

3'-TTCTACCAAAACCTTTACGA-5' (SEQ ID NO:1).

B. Example 2

Inhibition of Aromatase Expression

Semi-confluent JEG-3 cells, see, supra, were incubated in 2 charges in a standard medium for 14 hours each. The medium of one charge did not contain dbcAMP. See, supra. The cells are referred to as "untreated cells C" below. The medium of the other charge contained 1 mM of dbcAMP. These cells are referred to as "stimulated cells S" below.

Then, 100 µ/ml of the antisense oligonucleotide of Example 1 were added in each case three times to the untreated cells (C) and the stimulated cells (S). The additions were made 14, 16 and 18 hours after the time when dbcAMP had been added to the stimulated cells (S). 24 hours after the above time all cells were harvested separately and analyzed with respect to the following aspects:

(I) Aromatase mRNA (II) Aromatase activity; Aromatase protein

Figure 1B:
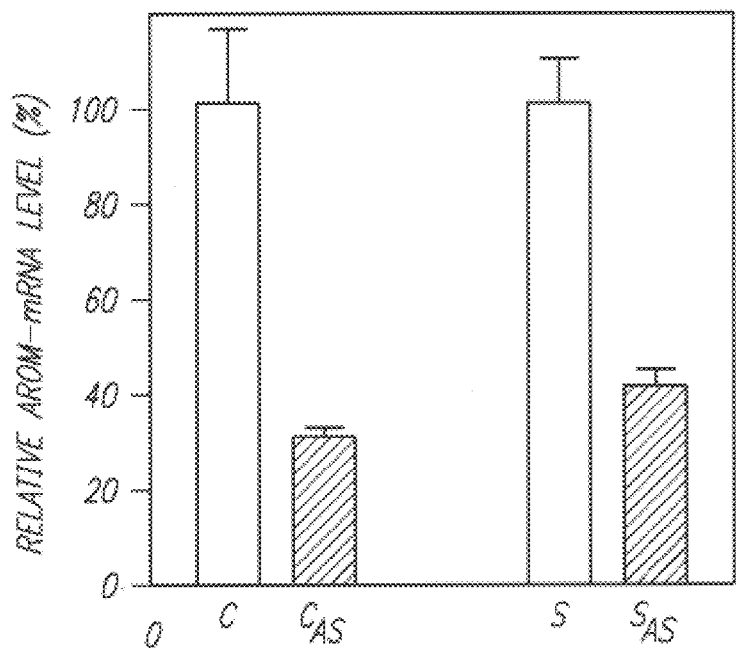
FIG. 1B depicts a densiometric quantification of the Northern Blot shown in FIG. 1A.

As to (I) Aromatase mRNA:

Entire RNA was isolated each from the harvested cells as usual. This RNA was analyzed twice (FIG. 1A and 1B):

(A) Northern Blot (FIG. 1A):

The RNA (12 µg) was subjected to a conventional Northern blot in which it was hybridized against an aromatase cDNA fragment which comprises exon II partially, exons III and IV completely as well as exon V partially (FIG. 1A, panel a). Furthermore, the RNA was hybridized against a glyceraldehyde-3-phosphate dehydrogenase (GAPDH) cDNA fragment as control (FIG. 1A, panel b). The indication C refers to untreated cells without antisense oligonucleotide, $^C$AS denotes untreated cells with antisense oligonucleotide, S represents stimulated cells without antisense oligonucleotide and $^S$AS stands for stimulated cells with antisense oligonucleotide.

(B) Densitometric quantification (FIG. 1B):

The autoradiography signals of aromatase mRNA in FIG. 1A were set to 100% in those cases in which no antisense oligonucleotide treatment (C, S open columns) was given and compared with the signals obtained in the case of cells with antisense oligonucleotide treatment ($^C$AS, $^S$AS; dashed columns).

Thus, FIG. 1A discloses that after the addition of the antisense oligonucleotide, the amount of aromatase mRNA was reduced by about 60%. Furthermore, an increased degradation of aromatase mRNA was affected.

Figure 2A:
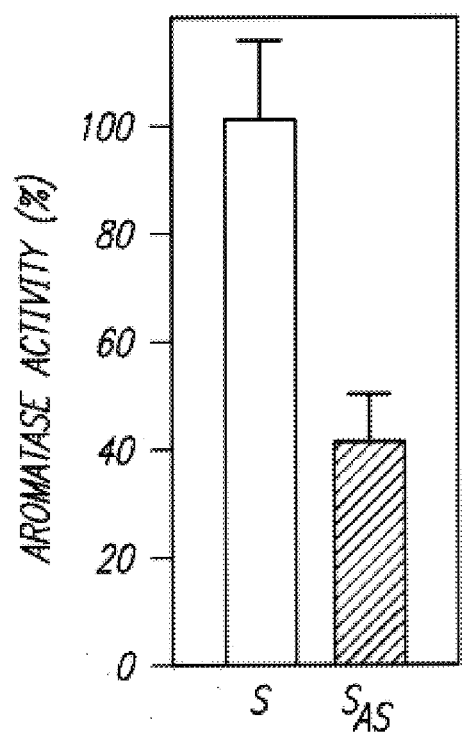
FIG. 2A depicts the effect of an antisense oligonucleotide according to the invention on the aromatase activity.

As to (II) Aromatase activity; Aromatase protein:

(A) Aromatase activity (FIG. 2A):

The harvested cells were taken up in a homogenization buffer, pH 7.4 (10 mM potassium phosphate, 150 mM KCL and 10 mM EDTA). The cells were opened up by ultrasonic treatment and microsomes were obtained after centrifugation of the homogenate at 10,000 g for 20 minutes and centrifugation of the resulting supernatant at 300,000 g for 20 minutes. They were resuspended in a reaction buffer, pH 7.4 (50 mM potassium phosphate, 2.5 mM glucose-6-phosphate, 0.25 U/ml glucose-6-phosphate dehydrogenase and 10 $\mu$M testosterone as substrate). The mixture was incubated at 37° C. for 5 minutes, and the reaction was started by adding NADPH up to a final concentration of 100 $\mu$M. After 5 hours, the reaction was stopped by 5-minute heating to 95° C. and the formation of 17β estradiol was determined by a competitive E2 enzyme immunoassay kit (Dianova). In FIG. 2A, the indication S refers to stimulated cells without antisense oligonucleotide and $^S$AS are stimulated cells with antisense oligonucleotide. The former were set to be 100%.

(B) Aromatase protein (FIG. 2B):

70 $\mu$g protein each were inserted from the microsomes in an SDS page. Then, the protein was transferred to a PVDF membrane, and the aromatase protein was identified by a generally available, monospecific polyclonal aromatase antibody.

Figure 2B:
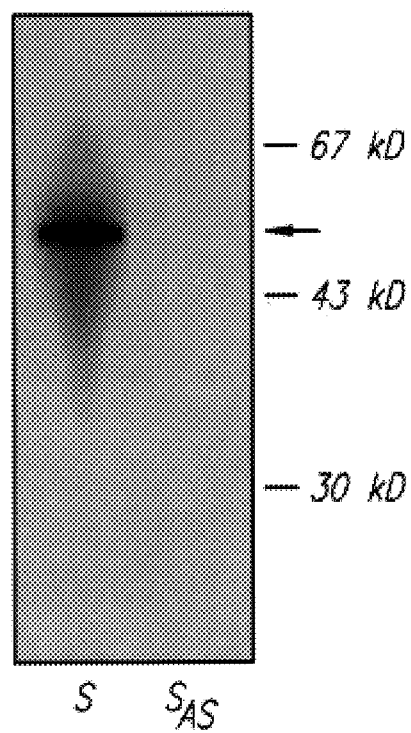
FIG. 2B depicts the effect of an antisense oligonucleotide according to the invention on the aromatase protein.

Thus, FIGS. 2A and 2B discloses that after the addition of the antisense oligonucleotide the aromatase activity was reduced by about 60%. In addition, non-identification of the aromatase protein was affected in a Western blot.

All references cited within the body of the instant specification are hereby incorporated by reference in their entirety.

What is claimed:

1. An antisense oligonucleotide, said antisense oligonucleotide consisting of the sequence:

3'-TTCTACCAAAACCTTTACGA-5' (SEQ ID NO:1).

2. An antisense oligonucleotide, said antisense oligonucleotide consisting of the sequence:

3'-CCTCCCGACTTGTGCACCTC-5' (SEQ ID NO:2).

* * * * *